United States Patent [19]
Bott

[11] Patent Number: 5,167,479
[45] Date of Patent: * Dec. 1, 1992

[54] CARGO RESTRAINT SYSTEM

[76] Inventor: John A. Bott, 931 Lakeshore Dr., Grosse Pointe Shores, Mich. 48236

[ * ] Notice: The portion of the term of this patent subsequent to Jul. 30, 2008 has been disclaimed.

[21] Appl. No.: 728,552

[22] Filed: Jul. 11, 1991

Related U.S. Application Data

[63] Continuation of Ser. No. 496,115, Mar. 19, 1990, Pat. No. 5,035,184, which is a continuation of Ser. No. 251,033, Sep. 26, 1988, abandoned, which is a continuation of Ser. No. 21,778, Mar. 4, 1987, abandoned.

[51] Int. Cl.$^5$ .............................................. B60P 7/135
[52] U.S. Cl. ..................................... 410/121; 410/130
[58] Field of Search ............... 410/135, 130, 129, 132, 410/133, 139, 121, 140, 118; 108/10, 137, 129, 132; 211/85, 162, 195; 224/42.42, 273, 311, 326; 248/297.2, 298; 296/37.5, 37.16

[56] References Cited

U.S. PATENT DOCUMENTS

| Re. 28,788 | 4/1976 | Williamson, III . |
| 907,171 | 12/1908 | Knight .......................... 211/195 X |
| 1,499,229 | 6/1924 | Laffey . |
| 1,875,772 | 9/1932 | Strathaus . |
| 2,388,304 | 11/1945 | Ackerman et al. . |
| 2,518,342 | 8/1950 | Lim . |
| 2,808,788 | 10/1957 | Stough . |
| 2,986,315 | 5/1961 | Zimmerman . |
| 3,164,395 | 1/1965 | Burch et al. . |
| 3,193,122 | 7/1965 | Sauthoff . |
| 3,203,363 | 8/1965 | Miller . |
| 3,229,994 | 1/1966 | Klein . |
| 3,428,330 | 2/1969 | Klein . |
| 3,446,526 | 5/1969 | Peters . |
| 3,620,171 | 11/1971 | Brenia et al. . |
| 3,643,973 | 2/1972 | Bott . |
| 3,779,174 | 12/1973 | Doyle et al. . |
| 3,845,601 | 11/1974 | Kostecky . |
| 4,029,244 | 6/1977 | Roberts . |
| 4,049,311 | 9/1977 | Dietrich et al. . |
| 4,181,349 | 1/1980 | Nix et al. . |
| 4,185,799 | 1/1980 | Richards, Jr. . |
| 4,200,046 | 4/1980 | Koliba et al. . |
| 4,226,348 | 10/1980 | Dottor et al. . |
| 4,278,376 | 7/1981 | Hunter . |
| 4,341,412 | 7/1982 | Wayne . |
| 4,500,020 | 2/1985 | Rasor . |
| 4,507,033 | 3/1985 | Boyd . |
| 4,536,025 | 8/1985 | Yamawaki et al. . |
| 4,540,213 | 9/1985 | Herlitz et al. . |
| 4,592,530 | 6/1986 | Seely et al. ..................... 248/298 X |
| 4,717,298 | 1/1988 | Bott . |
| 4,875,730 | 10/1989 | Justice ............................ 410/135 X |
| 4,887,947 | 12/1989 | Bott .................................. 410/129 X |
| 4,955,771 | 9/1990 | Bott .................................. 410/130 X |

FOREIGN PATENT DOCUMENTS

| 540442 | 5/1957 | Canada . |
| 1161214 | 8/1958 | France . |
| 2395861 | 6/1978 | France . |
| 1588292 | 4/1981 | United Kingdom . |

Primary Examiner—Margaret A. Focarino
Assistant Examiner—Gary C. Hoge
Attorney, Agent, or Firm—Harness, Dickey & Pierce

[57] ABSTRACT

A cargo restraint system for vehicles is disclosed. The cargo restraining devices includes a mechanism secured to a vehicle surface to enable selectable positioning of the cargo restraint system. Also, a member for restraining cargo on the vehicle surface is associated with the selectable positioning mechanism secured to the vehicle surface. The restraining member is movable from a first position, substantially parallel with and adjacent to the vehicle surface, to a second operable position. In the operable second position, the restraining member is substantially orthogonal to the vehicle surface.

9 Claims, 3 Drawing Sheets

CARGO RESTRAINT SYSTEM

This is a continuation of application Ser. No. 07/496,115, filed Mar. 19, 1990, now U.S. Pat. No. 5,035,184, which is a continuation of Ser. No. 07/251,033, filed Sep. 26, 1988, now abandoned, which is a continuation of Ser. No. 07/021,778, filed Mar. 4, 1987, now abandoned.

BACKGROUND AND SUMMARY OF THE INVENTION

The present invention relates to vehicles and, more particularly, to cargo restraint systems positioned on a vehicle surface.

As vans and mini vans become more predominant in society, a need arises to stabilize cargo positioned in the rear of these vehicles. Even in station wagons and conventional vehicle trunks, a device is needed for stabilizing and restraining cargo positioned in these vehicles. Thus, there is a need in the field for a cargo restraint which prevents groceries, or the like, from sliding around in the open rear cargo area of a vehicle. A desired cargo restraint system should be selectively positionable in an operable position, enabling restraint of groceries, cargo, or the like, to a non-operable position where the cargo restraining system is out of the way, enabling other uses of the open rear cargo area. Thus, there is a need in the field for a cargo restraining system which meets these desired characteristics.

Accordingly, the present invention meets the needs of the above described cargo system. The present invention provides the art with a cargo restraint system which is selectively movable from an operable position to an out of the way non-operable position. The present invention provides a vehicle with a cargo restraint device which divides the cargo area into desired partitions. The present invention provides the art with an easily installed cargo restraint system that is both practical and economical in use.

The present invention provides the art with a new cargo restraint system. The present invention includes a mechanism secured to a vehicle surface for enabling selectable positioning of the cargo restraint system. A member for restraining cargo on the vehicle surface is associated with the mechanism secured to the vehicle surface. The member for restraining cargo is movable from a first non-operable position, substantially parallel and adjacent to the vehicle surface, to a second operable position. In the operable position, the restraint member is substantially perpendicular to the vehicle surface for restraining cargo.

The mechanism for enabling selectable positioning of the cargo restraint system generally includes one or more track members secured to the surface of the vehicle. Also, a slider member is associated with each of the track members. The slider members selectively position the cargo restraint member along the track members for dividing the cargo area.

From the subsequent description and appended claims taken in conjunction with the accompanying drawings, other objects and advantages of the present invention will become apparent to one skilled in the art.

DETAILED DESCRIPTION OF THE PREFERRED EMBODIMENT

Figure 1:
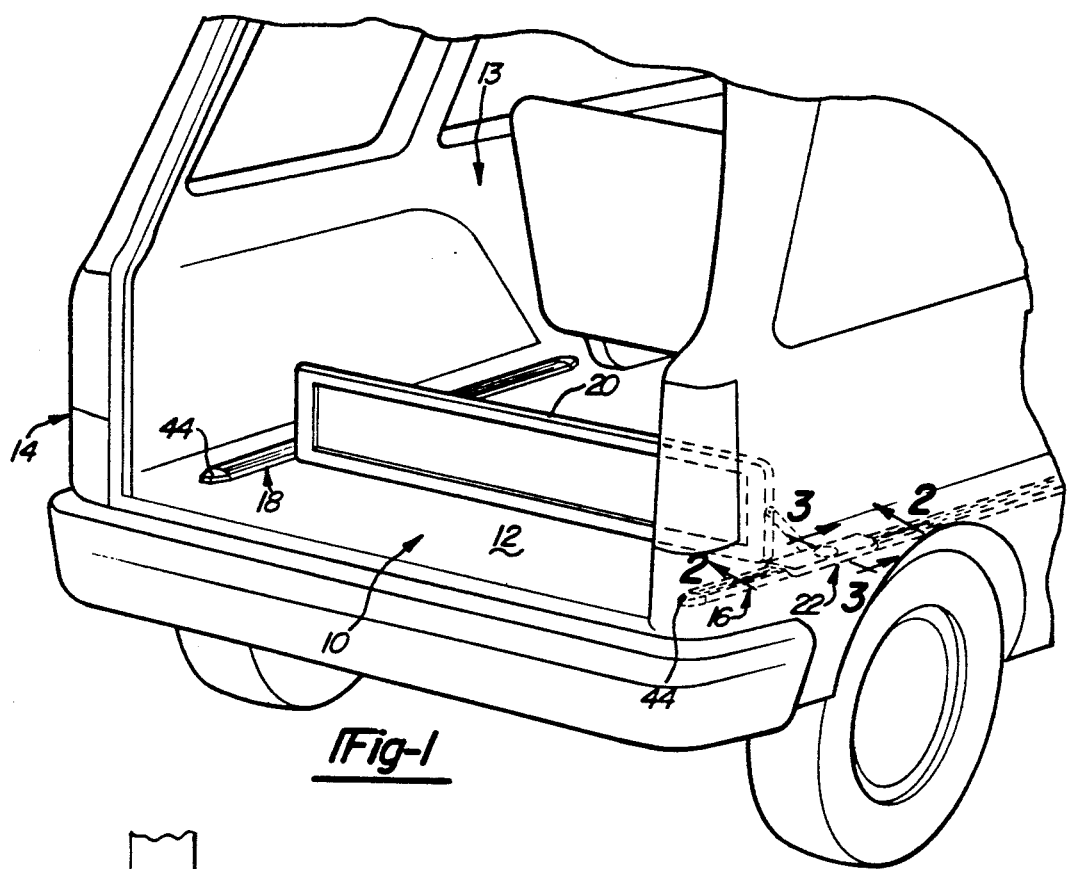
FIG. 1 is a perspective view of a cargo restraint system in accordance with the present invention.

Referring to the figures, a cargo restraint system is illustrated and designated with the reference numeral 10. Generally, the cargo restraint system is positioned in the cargo area 13 of a vehicle 14. The cargo restraint system 10 generally includes a pair of track members 16 and 18 secured to the vehicle surface 12 to enable selectable positioning of a beam member 20 of the cargo restraint system 10. The beam member 20 is associated with the track members 16 and 18 by slider mechanisms 22. The beam member 20 enables groceries, cargo, or the like, to be retained in a selected desired position on either side of the beam member 20. Preferably, the groceries, cargo, or the like, are supported by the beam member 20 on either side of the beam member 20 such that the seat or hatchback lid, supports the other side of the groceries, cargo, or the like. The beam member 20 is shown in FIG. 1 in its operable position extending substantially orthogonal or perpendicular to the vehicle surface 12.

The tracks 16 and 18 are elongated members generally secured to the vehicle surface 12 by conventional means, such as bolts. The track members 16 and 18 have an overall rectangular cross section with a pair of projecting flanges 24 and 26. A channel 28 is formed in the track members 16 and 18 and is associated with an opening 30 on top of the track members 16 and 18. The track members 16 and 18 have a sunken bottom portion 40 having a plurality of depressions 42. The depressions 42 enable the slider mechanism to be secured therein to select a desired position of the beam member 20. The depressions 42 act as detents to enable the sliding mechanisms 22 to ratchet along in the track channel 28. Also, an end cap 44 may be positioned in the channel 28 for retaining the slider mechanism 22 within the track channel 28.

The flange members 24 and 26 project from the opening 30 and bend so that they are parallel to the lateral sides 32 and 34 of the track members 16 and 18. The flanges 24 and 26 again bend inward, and extend parallel to the top and bottom 40 of the track members 16 and 18. Gaps 36 and 38 are formed between the track side walls 32 and 34 and the flanges 24 and 26.

Figure 2:
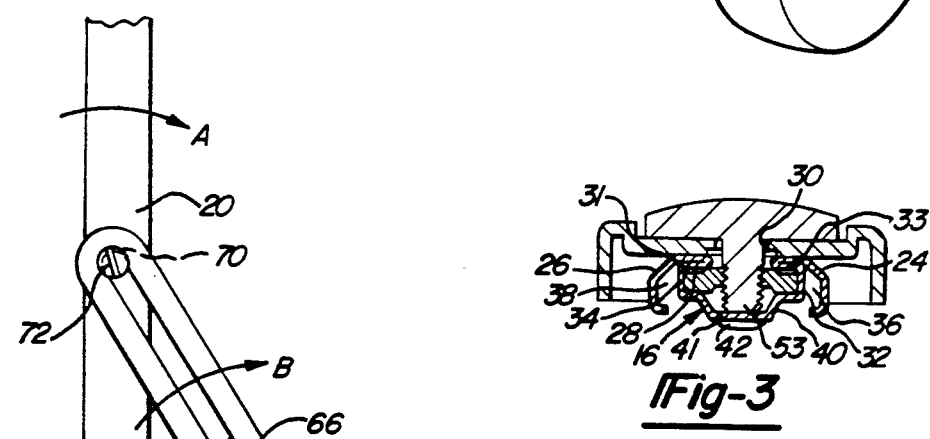
FIG. 2 is a partial cross-section view of FIG. 1 along line 2—2 thereof.
Figure 3:
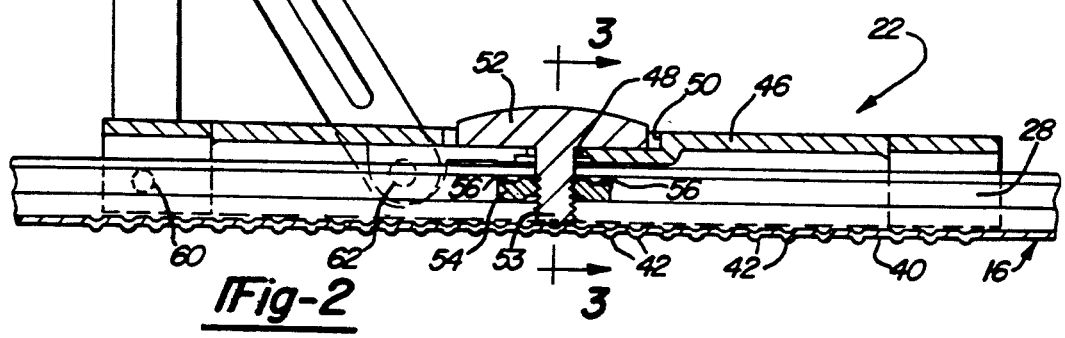
FIG. 3 is a cross-section view of FIG. 1 along line 3—3 thereof.
Figure 4:
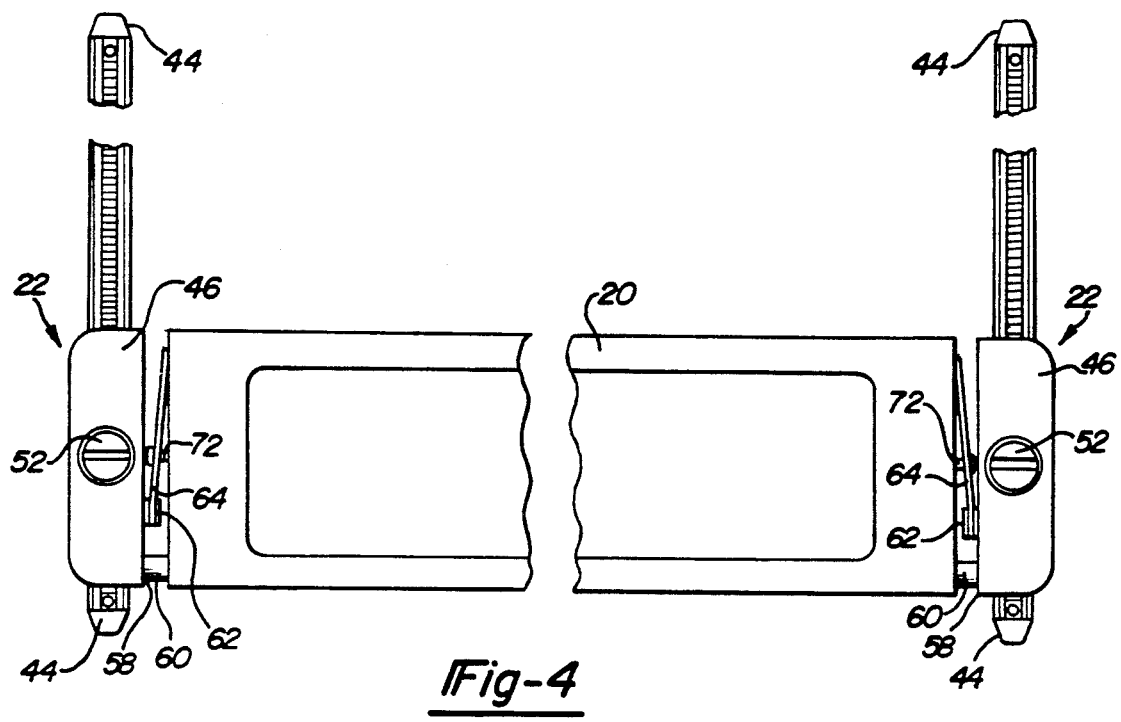
FIG. 4 is a plan view of FIG. 1 in a non-use position.

Turning to FIG. 2, a slider mechanism 22, shown in cross-section, is positioned on a track member. The slider mechanism 22 includes a base 46 having an overall rectangular shape with curved ends. An aperture 48 and counter sink 50 are formed in the base 46. The aperture 48 and counter sink 50 enable a fastener member 52 to pass through the aperture 48 and seat in the counter sink 50. The fastener member 52 is associated with a tap plate 54 positioned within the track channel 28. As the fastener member 52 is tightened in the tap plate 54, the tap plate 54, having projections 56, contacts the inside top surface of the track members. This contacting locks the tap plate 54 against the track top surface and secures the slider mechanism 22 in a desired position along the track members 16 and 18. The base 46 has a recess 58 for enabling a pin 60, associated with the beam member 20, to seat in the recess 58. The beam member 20, via the pin 60, is rotatably secured in the base recess. A second pin 62, secured in the base member 46, enables a bracket 64 to be associated with the base 46. The bracket 64 is also associated with the beam member 20.

The bracket 64 has an overall elongated rectangular shape and a slot 66 substantially through the bracket 64. The bracket 64 also has an aperture for enabling the bracket 64 to be pivotally secured to the base 46 by pin 62. The slot 66 has an enlarged circular portion 70 at the end furthest away from the aperture. The circular portion 70 enables a pin 72, secured to the beam member 20, to become locked in the bracket 64 when the beam member 20 is placed in its operable position perpendicular to the vehicle surface 12.

The beam member 20 has an overall rectangular shape and is associated with the slider bases 46 via pins 60. The beam member 20 is generally a relatively flat planar member possibly having depressions therein for enhancing manufacturing of the base member 20. The beam member 20 may be manufactured from plastic, wood, metalic material, or a combination thereof. The beam member 20 is manufactured by conventional means.

Figure 5:
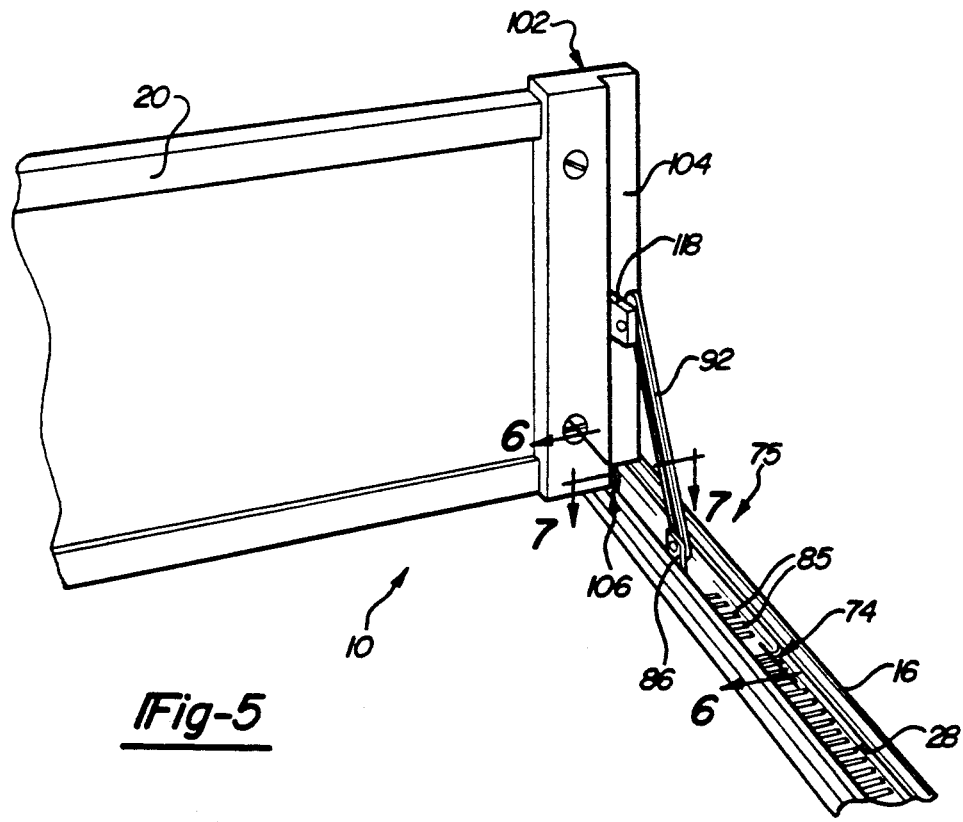
FIG. 5 is a partial perspective view of another embodiment of a cargo restraint system in accordance with the present invention.
Figure 6:
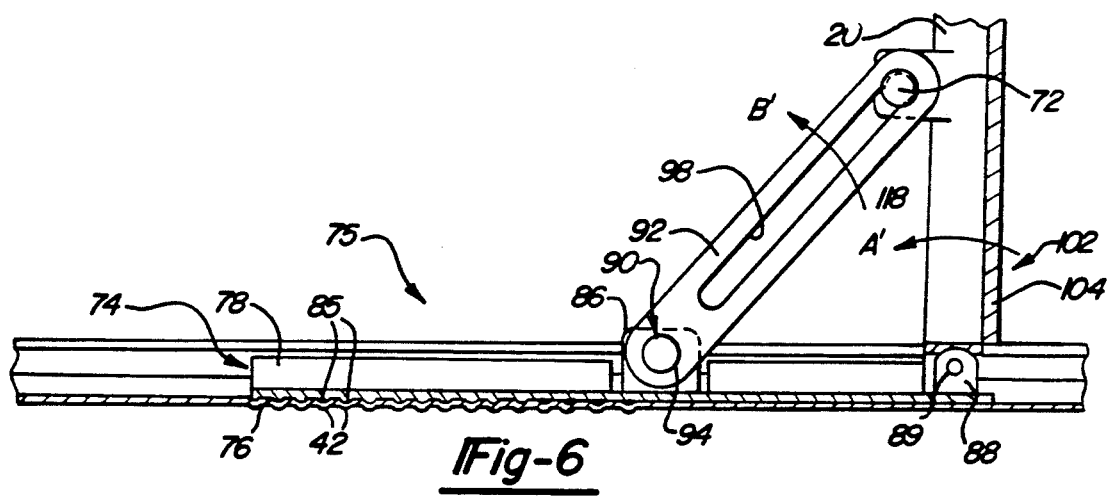
FIG. 6 is a partial cross-section view of FIG. 5 along line 6—6 thereof.

Moving to FIG. 5, a second embodiment of the present invention is shown. The elements which are substantially similar to the elements of the first embodiment will be numbered with the same reference numeral. The differences between the embodiments will be pointed out.

The cargo restraint system 10 includes track members 16 and 18 which are substantially the same as those in the first embodiment. Also, the beam member 20 is substantially the same as that in the first embodiment. The slider mechanisms 75 of the second embodiment differs from the slider mechanism 22 of the first embodiment.

Figure 7:
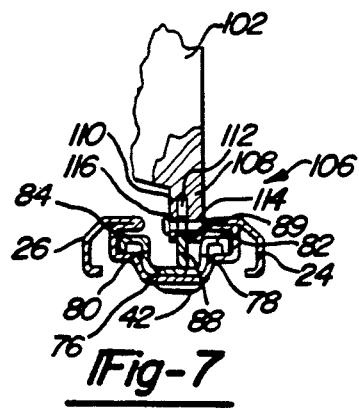
FIG. 7 is a cross-section view of FIG. 5 along line 7—7 thereof.

The slider mechanisms 75 includes a frame member 74 positioned within the track channel 28. The frame member 74 includes a bottom 76 having a pair of extending side walls 78 and 80 as seen in FIG. 7. A pair of flanges 82 and 84 extend from the side walls 78 and 80 substantially parallel to the bottom 76. Thus in cross section, the frame member 74 has a U-shaped cross-section appearance with the flanges 82 and 84 extending perpendicular to the free ends of the "U" as seen in FIG. 7. The bottom 76 has one or more nubs 85 extending therefrom. The nubs 85 nest in the track depressions 42 to secure the frame 74 in a selected position along the track members 16 and 18. The frame member 74 also includes extending members 86 and 88 to secure bracket 92 and the beam member 20, respectively, onto the frame member 74.

Projecting member 86 extends from side wall 78 substantially perpendicular to the frame bottom 76. Projecting member 86 has an aperture 90 to enable passage of a rivet, or the like, to secure the bracket 92 onto the frame member 74. The bracket 92 is substantially the same as bracket 64 but varies in some aspects, as will be pointed out herein.

The bracket 92 has an aperture 94 to secure the bracket 92 by conventional means, such as a rivet or the like, to the projecting member 86. The bracket member 92 has an angled end 96 which provides the bracket 92 with resilient spring characteristics. The bracket 92 also has a longitudinal slot 98 running substantially through the entire bracket 92. The slot 98 has an enlarged circular portion 100 at one of its ends. The slot circular portion 100 enables the bracket 92 to lock the beam pin 72 in the bracket 92 when the beam member 20 is in its operable position.

Figure 8:
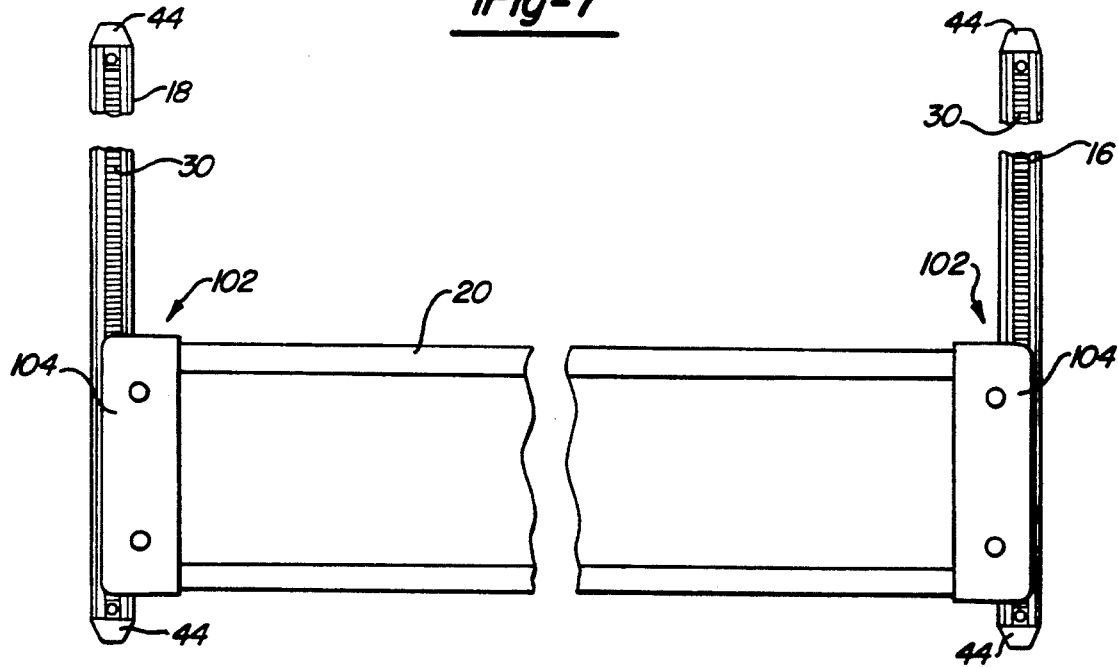
FIG. 8 is a plan view of FIG. 5 in a non-use position.

Beam member 20 has end caps 102 secured to the ends of the beam member 20. The end caps 102 have a projecting flange 104 extending parallel with and away from the beam member 20. The flange 104 covers the track opening 30 when the beam member 20 is in its nonoperable position, as shown in FIG. 8. The flange 104 has a member 106 to connect the end cap 102 to the frame member projection 88. Member 106 includes a pair of walls 108 and 110 having a slot 112 between the walls 108 and 110, as seen in FIG. 7. The walls 108 and 110 have apertures 114 and 116 therethrough corresponding with aperture 89 in projecting member 88. A fastener, such as a rivet or the like, is passed through apertures 114, 89, and 116, to secure the end cap 102 and the beam member 20 onto the slider frame member 74.

The end cap 102 also has an extending bracket 118 to secure beam pin 72 onto the end cap 102. The pin 72 is secured to the bracket portion 118 of the end cap 102. The pin 72 enables pivotal movement of the beam member 20 from its non-operable position, adjacent to the vehicle surface 12, to its operable position substantially perpendicular to the vehicle surface 12. When the beam member 20 is in its non-operable position, as shown in FIG. 8, the bracket 118 is positioned through opening 30 in the track channel 28. Also, the flange 104 covers the brackets 92 and 118 to provide the cargo restraint assembly with hidden hardware in its non-operable position.

While the above summarizes the present invention, it will become apparent to one skilled in the art that modifications, variations, and alterations may be made to the present invention without deviating from the scope and fair meaning of the subjoined claims.

What is claimed is:

1. A cargo restraint for a vehicle comprising:

a planar wall member for restraining movement of cargo on a vehicle surface, said wall member having a pair of opposite lateral edges and being movable from a retracted, non-restraining, first position wherein said wall member is substantially parallel to said vehicle surface and adjacent a positioning means to a restraining, second position wherein said wall member is substantially perpendicular to said vehicle surface for restraining movement of said cargo;

said positioning means including longitudinal track means fixedly secured to a vehicle surface for enabling selectable, slidable positioning of said planar wall member above said vehicle surface;

slider means slidably associated with said track means for further enabling selectable positioning of said planar wall member;

bracket means pivotally coupled with said slider means and said planar wall member for enabling said planar wall member to be moved into said first and second positions;

first pivot means for pivotally coupling said bracket and said planar wall member and for enabling said planar wall member to move pivotally relative to said bracket means; and second pivot means for pivotally coupling said bracket and said slider means, and movable with said slider means for enabling said bracket means to move pivotally relative to said slider means;

said first and second pivot means and said bracket means cooperating to enable said planar wall member to be moved between said first and second positions.

2. The cargo restraint of claim 1, wherein said slider means includes a base positioned about the exterior of said track member and a securement member associated with said base for removably securing said base to said track member.

3. The cargo restraint of claim 2, wherein said base includes means for pivotally securing said pivot means to said base.

4. The cargo restraint of claim 1, wherein said slider means includes a frame member positioned within said track member and means on said frame member for securing said frame member in position in said track member.

5. The cargo restraint of claim 4, wherein said frame member includes means for pivotally securing said pivot means to said frame member.

6. A method for adjustably restraining cargo in a cargo area of a vehicle wherein said vehicle includes at least one pair of generally parallel extending track members secured to a generally horizontal surface of said cargo area, a restraining beam member, a bracket member pivotally coupled to said restraining beam member at a first pivot point and sliding means pivotally coupled to said bracket member at a second pivot point and slidably positionable along said track members for adjustably positioning said restraining beam member at a desired position along said track members and enabling said restraining beam member to be moved pivotally between an upright restraining position and a folded, non-restraining position, and means for locking said sliding means at said desired positions, said method comprising the steps of:

moving said restraining beam member pivotally about said bracket member at said first pivot point while simultaneously moving said bracket member pivotally relative to said sliding means about said second pivot point to cause said restraining beam member to be moved into said upright restraining position from said folded, non-restraining position;

slidably moving said sliding means, said bracket member and said restraining beam member to said desired position along said track members; and locking said sliding means at said desired position to thereby maintain said restraining beam member in said desired position.

7. The method of claim 6, further comprising:
unlocking said sliding means;
slidably moving said sliding means and said restraining beam member away from cargo disposed within said cargo area; and
removing said cargo.

8. The method of claim 6, further comprising:
pivotally moving said restraining beam member from said upright restraining position to said folded, non-restraining position;
moving said sliding means along said track members and said restraining beam member to a desired storage position; and
locking said sliding means at said desired storage position.

9. A cargo restraint for a vehicle comprising:
a planar wall member for restraining movement of cargo on a vehicle surface, said wall member having a pair of opposite lateral edges and being movable from a retracted, non-restraining, first position wherein said wall member is substantially parallel to said vehicle surface and adjacent a positioning means to a restraining, second position wherein said wall member is substantially perpendicular to said vehicle surface for restraining movement of said cargo;

said positioning means including longitudinal track means fixedly secured to a vehicle surface for enabling selectable, slidable positioning of said planar wall member above said vehicle surface;

slider means slidably associated with said track means for further enabling selectable positioning of said planar wall member;

bracket means pivotally coupled with said slider means and said planar wall member for enabling said planar wall member to be moved into said first and second positions;

first pivot means for pivotally coupling said bracket and said planar wall member and for enabling said planar wall member to move pivotally relative to said bracket means; and second pivot means for pivotally coupling said bracket and said slider means, and movable with said slider means for enabling said bracket means to move pivotally relative to said slider means; and third pivot means for pivotally coupling an end portion of said planar wall member with said slider means;

said first, second and third pivot means and said bracket means cooperating to enable said planar wall member to be moved between said first and second positions.

* * * * *